US009517053B2

(12) United States Patent
Sinelnikov

(10) Patent No.: US 9,517,053 B2
(45) Date of Patent: Dec. 13, 2016

(54) DUAL-MODE PIEZOCOMPOSITE ULTRASONIC TRANSDUCER

(71) Applicant: MISONIX, INCORPORATED, Farmingdale, NY (US)

(72) Inventor: Yegor Sinelnikov, Port Jefferson, NY (US)

(73) Assignee: MISONIX, INCORPORATED, Farmingdale, NY (US)

(*) Notice: Subject to any disclaimer, the term of this patent is extended or adjusted under 35 U.S.C. 154(b) by 421 days.

(21) Appl. No.: 14/192,489

(22) Filed: Feb. 27, 2014

(65) Prior Publication Data

US 2014/0180103 A1   Jun. 26, 2014

Related U.S. Application Data

(63) Continuation of application No. 13/201,416, filed as application No. PCT/US2011/000910 on May 20, 2011, now Pat. No. 8,698,377.

(60) Provisional application No. 61/396,111, filed on May 21, 2010.

(51) Int. Cl.
| | |
|---|---|
| H01L 41/08 | (2006.01) |
| B06B 1/06 | (2006.01) |
| A61B 8/00 | (2006.01) |
| A61N 7/00 | (2006.01) |
| A61N 7/02 | (2006.01) |
| H01L 41/09 | (2006.01) |
| A61B 8/08 | (2006.01) |
| A61B 18/00 | (2006.01) |

(52) U.S. Cl.
CPC ........... *A61B 8/4483* (2013.01); *A61B 8/4494* (2013.01); *A61B 8/485* (2013.01); *A61N 7/00* (2013.01); *A61N 7/02* (2013.01); *B06B 1/0629* (2013.01); *H01L 41/09* (2013.01); *A61B 2018/0016* (2013.01); *A61B 2018/00577* (2013.01); *A61B 2090/378* (2016.02); *A61N 2007/0078* (2013.01)

(58) Field of Classification Search
CPC ..... G10K 11/02; B06B 1/0622; B06B 1/0629; B06B 1/067
USPC ................ 310/322, 326, 327, 334, 357, 367
See application file for complete search history.

(56) References Cited

U.S. PATENT DOCUMENTS

| | | | |
|---|---|---|---|
| 4,356,422 A | 10/1982 | van Maanen | ................. 310/322 |
| 5,316,000 A | 5/1994 | Chapelon et al. | |
| (Continued) | | | |

FOREIGN PATENT DOCUMENTS

| | | | | |
|---|---|---|---|---|
| DE | 3441563 A1 | * | 11/1984 | ............... B06B 1/06 |
| FR | 2634089 A | * | 1/1990 | ............... B06B 1/06 |

OTHER PUBLICATIONS

US 4,950,636, 08/1990, Rynne et al. (withdrawn)

*Primary Examiner* — Thomas Dougherty
(74) *Attorney, Agent, or Firm* — R. Neil Sudol; Henry D. Coleman

(57) ABSTRACT

A compact, high power, dual mode, emitting and receiving ultrasound transducer and method for applying ultrasonic energy within a living subject and for monitoring the effects it induces in tissue comprises a set of piezoelectric polymeric transducer elements and a set of piezoelectric ceramic elements, bonded together. The polymeric transducer elements have electrodes enabling their use for low power diagnostic imaging interrogation of the tissue and the ceramic transducer elements have electrodes enabling their use for high power therapy applications.

29 Claims, 7 Drawing Sheets

(56) References Cited

U.S. PATENT DOCUMENTS

| | | | |
|---|---|---|---|
| 5,389,848 A * | 2/1995 | Trzaskos | B06B 1/0611 310/322 |
| 5,558,092 A | 9/1996 | Unger et al. | |
| 5,702,629 A | 12/1997 | Cui et al. | 252/62.9 R |
| 6,810,604 B2 | 11/2004 | Chen et al. | 36/14 |
| 7,211,060 B1 | 5/2007 | Talish et al. | 602/2 |
| 7,652,410 B2 | 1/2010 | Prus | |
| 7,963,919 B2 | 6/2011 | Proulx et al. | 600/447 |
| 2002/0007118 A1 | 1/2002 | Adachi et al. | 600/443 |
| 2002/0135273 A1 | 9/2002 | Mauchamp et al. | 310/334 |
| 2003/0073906 A1 | 4/2003 | Flesch et al. | 600/459 |
| 2005/0234438 A1* | 10/2005 | Mast | A61N 7/02 606/27 |
| 2006/0184022 A1 | 8/2006 | Johnson | 600/437 |
| 2009/0216128 A1 | 8/2009 | Sarvazyan | |
| 2009/0240148 A1 | 9/2009 | Jeong et al. | |
| 2013/0002094 A1 | 1/2013 | Toda et al. | 310/327 |

* cited by examiner

DUAL-MODE PIEZOCOMPOSITE ULTRASONIC TRANSDUCER

CROSS-REFERENCE TO RELATED APPLICATIONS

This application is a continuation of U.S. patent application Ser. No. 13/201,416 filed Aug. 12, 2011, now U.S. Pat. No. 8,698,377. Application Ser. No. 13/201,416 was filed as a U.S. national phase of International Patent Application No. PCT/US11/00910 filed May 20, 2011. This application also claims the benefit of U.S. Provisional Patent Application No. 61/396,111 filed May 21, 2010.

FIELD OF INVENTION

The present invention relates to ultrasonic transducers.

BACKGROUND OF THE INVENTION

This invention is directed in principal part to an ultrasonic transducer device. More particularly, this invention is directed to a dual mode ultrasonic transducer device, one that can be used for both diagnostic investigations and therapy.

Ultrasound is widely used in modem medicine for diagnostics and treatment in such fields as obstetrics, cardiology, endocrinology, gastroenterology, neurology, ophthalmology, urology, osteoporosis, and clinical diagnostics. A wide range of clinical trials are being conducted for breast tumor ablation, urine fibroids ablation, benign prostatic hyperplasia ablation, fibrillation, cardiac, bleeding control, and brain disorder treatments (Clement, 2004, Perspectives in clinical uses of high intensity focused ultrasound, *Ultrasonics*, 42, 1087-1093).

Ultrasound diagnostics uses low-power ultrasonic scanners for investigation and visualization of inner organs, layers and structures, for determination of blood flow direction and velocity, for measurement of density and other parameters of tissues, and for detection of cancer and other tumors. Following an ALARA (as low as reasonably achievable) principle, diagnostic evaluation spatial peak temporal average intensities do not exceed 100 mW/cm$^2$ (Kremkau 2006, Diagnostic ultrasound: principles and instruments, 7$^{th}$ ed. Philadelphia Pa., Saunders).

Ultrasound propagating through the tissues attenuates and creates heat proportional to ultrasound intensity. The high intensity focused ultrasound (HIFU) can kill tissue through coagulative necrosis. This idea of HIFU for tissue necrosis and therapy actually predates its suggested use as a diagnostic tool. Nevertheless, it is only recently that therapeutic HIFU procedures have become practical and reliable, predominantly due to significant advances in ultrasound imaging technology over past decade that have enabled near real-time non-invasive monitoring and control of ultrasound treatment. At the same time, ultrasound guidance became a viable and low cost alternative to magnetic resonance imaging (MRI), X-ray computer tomography (CT). Ultrasound offers a credible potential to control the HIFU ablation process, and a number of ultrasound thermal imaging methods are currently under way to quantify HIFU induced temperature changes to tissue properties (e.g. Hill and Ter Haar, 1995, Review article: HIFU potential for cancer treatment. Br. J. Radiol, 68, 1296-1303; Zheng and Vaezy, 2010, An acoustic backscatter-based method for localization of lesions induced by HIFU, Ultrasound in Med & Biol, 36, 4, 610-622). Consequently, medical ultrasound imaging establishes itself as a vital component of the HIFU therapy, and gains clinical acceptance for a safe and effective tissue ablation and cancer therapy (Haar, 2010, Ultrasound bioeffects and safety, *Proceedings of the Institution of Mechanical Engineers, Part H: Journal of Engineering in Medicine*, 224 (2), pp. 363-373).

Being a subject of research for many year, ultrasound therapy only recently has found a widespread use in medical applications (ter Haar G, 2007, Therapeutic applications of ultrasound, Progress in Biophysics and Molecular Biology 93, 1-3, 2007, 111-129). Ultrasound therapy uses considerably higher ultrasound intensities than imaging. Levels up to 10 W/cm$^2$ are used for fast overheating of local areas of tissue. In hyperthermia treatment of cancer and tumors, the tissue is heated using ultrasound to temperatures of 43-45° C. for several minutes. Under such conditions tumor cells become much more susceptible to radiotherapy and chemotherapy. In physiotherapy ultrasound is used to increase the elasticity of sinews and scars, improve the mobility of joints, provide analgesic effects, alter blood flow, and produce muscular spasms. High intensity ultrasound (10-2000 W/cm$^2$) is used for tissue cutting, thermal ablation and for arresting internal bleeding (hemostasis) due to blood fibrillation. Piezoelectric and magnetostrictive transducers are widely used to transform an electrical current and voltage into mechanical oscillations that generate an ultrasound field.

Therapeutic ultrasound targets deep tissue using focused transducers with one or more active elements typically emitting continuous wave signals. Ultrasound can also be focused by manipulating the driving electrical signals (phase and amplitude) of multiple elements. (Cathignol, 2002, High Intensity Piezoelectric Sources for Medical Applications: Technical Aspects, *Nonlinear Acoustics at the Beginning of the 21$^{st}$ Century*, 1, 371-378.) Larger elements are more economical, but require mechanical steering and suffer a loss of acoustic efficiency due to the heating and presence of parasitic Lamb waves on their surfaces. (Kluiwstra et al., 1997, Design Strategies for Therapeutic Ultrasound Phased Arrays, SPIE International Medical Imaging Symposium). Properly energized and poled small elements are more economical but require complex circuitry. Resultant phased arrays comprising the small ultrasound elements can steer acoustic focus electronically, with most of the complexity, cost and associated quality assurance activity being shifted to assembly processes and driving system manufacturing.

It is to be noted that diagnostic imaging imposes a set of design requirements contradictory to a therapeutic mode of operation. While the continuous therapeutic mode favors narrow band, sharp resonant transducers for a high power output and improved efficiency over extended procedure time, the diagnostic mode relies predominantly on the pulse signals and favors broadband transducer design. A broader bandwidth results in more energy in short imaging pulses and translates into more sensitivity, yet broader bandwidth indicates less efficient vibration at resonance frequency. Because of these contrary requirements, spatially separated and individually operated therapeutic and imaging elements are used in conventional dual-mode HIFU applicators. Another imaging transducer design challenge is to match the acoustic impedance of about 33 MRyals, typical of PZT ceramics, to the relatively low 1.5 MRyals impedance of water or tissue in order to obtain a short impulse response and broad bandwidth. Typically, this impedance matching is accomplished by fabricating multi-stage close to quarter wave matching layers using epoxy resins loaded with tungsten or alumina powders. (Kosoff, 1966, The Effects of Backing and Matching on the Performance of Piezoelectric Ceramic Transducers, *IEEE Transactions on Sonics and Ultrasonics*, SU-13, 1, 20-30) Based on KLM transmission line models (Krimholtz, Leedom, Matthaie 1970, New Equivalent Circuits for Elementary Piezoelectric Transducers, *Electron Lett*, 6, 13, 398-399), the acoustic matching layers of imaging transducers should have impedances in the range of 8 to 15 MRyals. This is difficult but feasible to achieve using epoxy with sufficiently dense powder loading. Conversely, in the case of therapeutic transducers that operate near resonance to maximize surface vibration, the acoustic impedance of a matching layer should be much less than the impedance of the transducer material and water. Only few such practical low impedance materials available (Toda, 2002, Nanowband Impedance Matching Layer for High Efficiency Thickness Mode Ultrasonic Transducers, *IEEE Transactions on Ultrasonics, Ferroelectrics, and Frequency Control*, 49, 3), favoring the designs of therapeutic transducer without matching layers at all.

For most medical imaging ultrasonic applications one requires the large pulse amplitude for effective transmission through a body of a patient and good signal to noise ratio of the detected signal. This is especially important since biological tissues are attenuative or scattering materials. Also, the short pulse duration is necessary for good axial resolution, i.e. two signals in a short distance should be detected without interference. Consequently, in imaging transducers it appears desirable to dampen the vibration of the piezoelectric transducer material as quickly as possible to prevent ringing and multiple reflections. On the other hand, in therapeutic applications liquid cooled undampened sharp resonance transducers are typically used to produce acoustic signals of sufficient magnitude over a length of time. When using high power resonance transducers for imaging, improved power transmission leads to an improved imaging sensitivity, while ringing limits axial resolution. Vice versa, dampened transducers typically have lower power transmission and sensitivity on account of higher axial resolution. This trade off between power transmission and axial resolution presents another challenge for a design of single element transducer for simultaneous therapeutic and imaging application.

Thereby, multiple design constraints such as acoustic matching of high impedance ceramic transducers for broadband imaging and narrow band therapy, are fundamentally different, making the design and fabrication of the dual mode transducers for imaging and therapy extremely challenging.

At present, the ultrasound based imaging and Magnetic Resonance Imaging (MRI) are the competing modalities that offer a potential to evaluate the location of thermally induced lesions in a patient body. Due to restrictive technological complexity of combining HIFU and MRI, the real time ultrasound-based detection of the high lesions is favored. Some early methods relied on the speed of sound change with temperature to control the HIFU exposure (Miller, Bamber, Meaney, 2002, Functional limitation of non-invasive temperature imaging by means of ultrasound echo strain estimation. Ultrasound Med & Biol, 28, 1319-1333). However, the accuracy of this method is poor due to significant inter-patient variability, non-linear acoustic effects, thermal expansion, limited data available for different tissues. Other methods utilized the appearance of hyperechoic regions in B-mode imaging (Vaezy, Shi, Martin, Chi, Nelson, Bailey, Crum, 2001, Real-time visualization of HIFU treatment using ultrasound imaging, Ultrasound Med & Biol, 27, 33-42), which was only applicable when there was a significant cavitation.

Moreover, human body supports the propagation of many kinds of ultrasound waves, each of which can be used to acquire an image of internal organs. For example, compression waves reveal a tissue's density, while shear waves reveal tissue's elasticity. So called "harmonic imaging" has become common to ultrasonic medical diagnostics due to a higher resolution of the second harmonic in comparison with the fundamental frequency. The tissue response to harmonic vibration is characterized by Lamé parameters: $\lambda$, which is associated with the elastic resistance to volume change, and $\mu$, which characterizes the tissue's elastic resistance to shape change. A typical value for shear modulus $\mu$ is on the order of kPa, while a typical value for $\lambda$ is about 2.3 GPa, which is about six orders of magnitude higher than the shear modulus. In that limit, compression waves have a speed $\upsilon_p = \sqrt{(\lambda + 4/3\mu)} \approx \sqrt{\lambda 1 \rho} \approx 1500$ m/s and can propagate in ultrasound (megahertz) frequency range, while shear waves are characterized by significantly lower speed $\upsilon_s = \sqrt{\mu/\rho}$ and propagate at low sonic (kilohertz) frequencies. Because the soft tissue is 70-80% water, its resistance to volume change, $\lambda$, and density, $\rho$, do not vary much in comparison to $\mu$ (Sarvazyan A P, Rudenko O V, Swanson S D, Fowikes J B and Emelianov S Y, 1998, Shear wave elasticity imaging: a new ultrasonic technology of medical diagnostics. Ultrasound in Med. & Biol. 24 1419-1435). Consequently, shear waves can be a good tool for quantitative evaluation of deep-organs stiffness, providing an important palpatory diagnosis information. These, along with the aforementioned differences between imaging and therapeutic transducer design requirements, rapidly shifts a focus to the implementation of the nonlinear multiwave wave elastography in medical imaging and nondestructive testing (e.g. Fink and Tanter, 2010, Multiwave imaging and super resolution, Physics Today, 63, 2; Brysev et al, 2004, Nonlinear ultrasonic phase-conjugate beams and their application in ultrasonic imaging, Acoust. Phys. 50, 623-640; Mathias Fink. 2002, Acoustic Time-Reversal Mirrors. Topics Appl. Phys. 84, 17-43). Besides A-scan, B-scan, Doppler imaging, harmonic imaging, the recent advances also include contrast imaging, 3 and 4 dimensional imaging, coded excitation and elastography. The state of the art ultrasound systems use hundreds of piezoelectric transducers and ultrafast scanners (Sandrin L, Tauter M, Catheline S, Fink M. Shear modulus imaging with 2-D transient elastography, IEEE Trans Ultrason Ferroelectr Freq Control. 2002 April; 49(4):426-35.) to form a high-resolution image. Unlike conventional ultrasound imaging, where multiple bursts are required to produce an image, shear modulus imaging technique numerically reconstructs an image after each ultrasound transmission. The reconstruction process relies on the time reversal of the digitized compression back-scattered waveforms. A similar process has been described in a transient source time reversal acoustic holography (Sapozhnikov O A, Ponomarev A E and Smagin M A, Transient acoustic holography for reconstructing the particle velocity of the surface of an acoustic transducer, Acoustical Physics, 52, 3, 2006), which also showed that a quality of reconstruction depends on individual transducers' directivity. An array with ultrasound transducers having different directivities can substantially improve the accuracy of the time reversal imaging reconstruction or focusing. Transducers can be individually poled, either randomly or in an order sequence, and oriented in such a way that they sense a compressional wave coming from predefined direction. Alternatively, piezoelements can be made to sense both compressional and shear waves simultaneously. For example, 10° rotated Y-cut overtone-polished parallel-plated $LiNbO_3$ crystals were used as dual-mode source and receiver transducers in ultrasound interferometric measurements (Sinelnikov Y D; Chen G R; Liebermann R C, Dual mode ultrasonic interferometry in multi-anvil high pressure apparatus using single-crystal olivine as the pressure standard, High Pressure Research, 24, 1, 2004, 183-191).

It is also very desirable that the imaging array transducers have broad bandwidth and high sensitivity, and it is predicated on the ability to eliminate mechanical movement and deflect the beam electronically. Typically, imaging transducers are used both for generating the pulses and detecting respective echoes that arise when ultrasound pulses are partially reflected at boundaries between structures with different characteristic impedances. Elements of a group in an array can be excited in succession so that the ultrasound beam is electronically moved across the face of the transducer, providing an image similar to that obtained by scanning a single element transducer manually. An ability to steer and focus the acoustic energy at one or more locations simultaneously by manipulating the phase and amplitude of each element makes multiple elements ultrasound array attractive for therapeutic applications.

However, the material properties impose a significant constraint on the design of ultrasound imaging and therapeutic arrays. The conversion efficiency of the transducer indicates how well the transducer converts both the applied voltage into ultrasonic pressure pulse and the received echo into electrical voltage. Related to conversion efficiency, transducers' sensitivity is defined as the product of transmit and receive efficiencies. The sensitivity of a single element is largely defined by the piezoelectric material constants $d_{33}$ and $g_{33}$, which are indices of how well the material converts the voltage signal into mechanical deformations and the mechanical stress back into electrical voltage, respectively. Typically it is not feasible for both $d_{33}$ and $g_{33}$ constants to be large and typically a combination of closely spaced specially selected piezomaterials can be beneficially used in transmit and receive mode. The use of such piezocomposite materials becomes important for ultrasound guided HIFU therapy that relies on ultrasound accurate spatial localization of HIFU-induced lesions in real time and after HIFU exposures. The main objective shifts from the visualization of static internal organs of to the monitoring of target ablation process and providing a timely operator feedback for the treatment planning.

On the other hand, the success of the HIFU procedures depends on the intensity gain of the transducer, while the optimum imaging sensitivity, penetration, and ability for a similar dynamic focusing need to be preserved. In most designs the intensity is maximized by increasing the total power, which is proportional to a surface of emitting transducer. However, large transducers suffer from increased vibration and scattering losses, while a combination of small transducers is difficult to handle. One solution to obtain the high therapeutic intensity gain at a target is to arrange the therapy and imaging elements in a non-contiguous way. In such interleaved arrangement all array therapy and imaging elements point in the same direction, making the dynamic scanning region essentially similar for both arrays thus improving localization and temperature monitoring of the HIFU application. Such interleaved dual mode array will enable an improved multimode imaging that relies on a generation of the sufficiently high intensity of acoustic beam by therapeutic elements, necessary for generation of harmonics on a path of the backward propagation to the imaging elements.

SUMMARY OF THE INVENTION

The present invention aims in part to provide an improved ultrasonic transducer device. More particularly, the present invention aims in part to provide an ultrasound transducer device that is capable of effectively operating in a therapeutic mode and alternately in an imaging mode.

The present invention recognizes that the sensitivity of ultrasound imaging can be enhanced by using a combination of high power ceramic emitting transducers with high sensitivity polymeric broadband receiving transducers mechanically arranged and spatially contained in close proximity.

An ultrasonic transducer device in accordance with the present invention comprises at least one imaging transducer element made of a piezoelectric polymeric material and at least one therapeutic transducer element made of a piezoelectric ceramic material. The imaging transducer element and the therapeutic transducer element are bonded to one another, typically in direct contact and contiguous with one another. The bonded transducer elements may typically assume the form of an integrated and unitary transducer block or module.

In one embodiment of the present invention, the therapeutic transducer element is one of a plurality of piezoelectric ceramic transducer elements, all utilizable in a therapy (high voltage, high intensity) mode of operation. The ceramic transducer elements may be embedded in the imaging transducer element so that each of the ceramic transducer elements is spaced from the other ceramic transducer elements by the piezoelectric polymeric material. Thus, the ceramic therapy transducer elements are dispersed throughout a matrix of piezoelectric polymeric material.

In one or more embodiments, the piezoelectric ceramic transducer elements may be electrically independent from each other with at least a subset of those transducer elements being operable as a phased array while cross talk between members of the subset is minimized. The different piezoelectric ceramic transducer elements are connected via respective sets of electrical electrodes or contacts to respective leads connectable to a waveform generator that is generally under the control of a computer or microprocessor.

The imaging transducer element may be a single continuous substrate provided with a plurality of recesses, grooves, holes, cuts, dimples, or indentations hot pressed or filled with the piezoelectric ceramic material thereby forming the plurality of therapeutic elements.

The various transducer elements, both those for imaging and those for therapy, may have such substantially different excitation parameters that the transducers can be connected in parallel with one another in a single electrical circuit. As discussed in detail hereinafter, the ceramic transducers do not effectively register or detect the imaging waveforms owing to the low piezoelectric voltage constant, ringing and losses from impedance mismatch, while the polymeric transducers cannot transmit high-intensity waveforms due to low piezoelectric strain constant, high electrical impedance, large dielectric losses and temperature sensitivity.

In another embodiment of the present invention, the imaging transducer element is one of a plurality of piezoelectric polymeric transducer elements that are embedded in the therapeutic transducer element so that each of the piezoelectric polymeric transducer elements is spaced from the other piezoelectric polymeric transducer elements by the piezoelectric ceramic material. Again, the various transducer elements, both those for imaging and those for therapy, may be connected in parallel with one another in a single electrical circuit.

In at least one embodiment, the piezoelectric polymeric transducer elements are electrically independent from each other with at least a subset of those transducer elements being operable as a phased array while cross talk between members of the subset is minimized. The different piezoelectric polymeric transducer elements are connected via respective sets of electrical electrodes or contacts to respective leads connectable to a processor of ultrasonic echo signals that typically takes the form of a computer or microprocessor.

The therapeutic transducer element may be a single continuous substrate provided with a plurality of recesses, grooves, holes, cuts, dimples, or indentations filled with the piezoelectric polymeric material thereby forming the plurality of imaging elements. In a further embodiment of the present invention, the imaging transducer element is one of a plurality of piezoelectric polymeric transducer elements and the therapeutic transducer element is one of a plurality of piezoelectric ceramic transducer elements. The piezoelectric polymeric transducer elements and the piezoelectric ceramic transducer elements are bonded to one another so that each of the piezoelectric polymeric transducer elements is spaced from the other piezoelectric polymeric transducer elements by one or more of piezoelectric ceramic transducer elements and so that each of the piezoelectric ceramic transducer elements is spaced from other piezoelectric ceramic transducer elements by one or more of the piezoelectric polymeric transducer elements.

In an additional embodiment of the present invention, the imaging transducer element includes a plurality of first finger parts and the therapeutic transducer element includes a plurality of second finger parts. The first finger parts (imaging) and the second finger parts (therapy) are interdigitated or interleaved with one another so that each of the first finger parts is partially spaced from the other first finger parts by one or more of the second finger parts and so that each of the second finger parts is partially spaced from other second finger parts by one or more of the first finger parts. The first finger parts may be joined to one another at a bight or hand portion of the imaging transducer element. Similarly, the second finger parts may be joined to one another at a bight or hand portion of the therapeutic transducer element Pursuant to the above-described embodiments of the present invention, the invention provides in part a spatially distributed dual mode piezocomposite ultrasonic transducer for use in a medical therapy and imaging apparatus. More specifically, the invention provides a piezocomposite ultrasonic transducer composed of one or more piezoceramic transducer elements and one or more piezoelectric polymeric transducer elements that form an interpenetrant composite.

Piezocomposite materials are typically made up of fine small column of piezoelectric ceramic embedded in a polymer matrix (Smith and Auld, Modeling 1-3 composite piezoelectrics: thickness mode oscillations, IEEE Trans Ultrason Ferroelec Freq Contr, 1991, 38, 1, 40-47). Although the electroacoustical conversion efficiency of a piezocomposite transducer is a priori lower than that of a bulk ceramic transducer, there are explicit advantages offered by piezocomposite technology for the applications where multiple objectives are important:

lower acoustic impedance of piezocomposite and its thickness mode coupling coefficient larger than that of the ceramic materials facilitate the generation of a high intensity ultrasonic beam with wide frequency bandwidth;

strong anisotropy of piezocomposite materials leads to a reduction of parasitic surface modes, otherwise present in large scale plate or dome structures, a more homogeneous thickness mode vibration pattern, and enhanced acoustical independence of individual piezoceramic elements thus facilitating the design of multi-elements arrays.

geometric flexibility of piezocomposite designs permits a large adaptability to the form and fit constraints and enables production of miniaturized transducers for various extracorporeal, intracavity, intravascular and endoscopic applications.

spatially distributed piezocomposite transducers can be used in a diagnostic mode, applying ultrasonic energy within a body of living subject for visualization of body internal organs, and offer a potential to be used in a therapeutic applications, implementing thermal ablation, hyperthermia, transfection and/or ultrasound assisted drug delivery.

In one embodiment of the invention discussed above, an ultrasonically active portion of a transducer apparatus comprises a plurality of piezoceramic transducer elements embedded in a polymeric piezoelectric transducer matrix. Polymeric piezoelectric materials suitable for imaging transducer elements include polyvinylidene fluoride (PVDF), and copolymers of PVDF such as trifluoroethylene (TrFE) with a piezoelectric voltage constant $g_{33}>100\times10^{-3}$ Vm/N. An active polymer layer can be backed with polyurethane acoustic foam to permit a compact planar imaging array construction. The polymeric layers and acoustic foam backing constitute a structural-bonding element for the therapeutic transducers made of piezoceramic material, suitable for high power continuous ultrasound emission, including modifications of $BaTiO_3$, $Pb(Ti,Zr)O_3$ (PZT) and $PbNb_2O_6$ ceramics with a high piezoelectric strain constant, $d_{33}>200\times10^{-12}$ m/V. Such piezocomposite transducers offer several advantages over single crystal transducer designs (see U.S. Pat. No. 5,117,832 to Sanghvi et al., 1992), multi-layer transducer designs (U.S. Pat. No. 6,492,762 to Pant et al., 2002) and spatially distributed transducer designs (see U.S. Pat. No. 6,461,314 to Pant et al., 2002). These advantages include an enhanced therapeutic efficiency, a broad bandwidth, high transmit and receive efficiencies and consequently high sensitivity, and an ability to work in dual mode—therapy and imaging, implicit registration and alignment between the imaging and therapy elements, potential for miniaturization, cost reduction, improved manufacturability, and an ability to make a flexible transducer (Safari, 1992, Flexible Composite Transducers, *J. Am. Ceram. Soc.*, 65: 207-209).

Typical piezocomposite material used in underwater and medical acoustics consists of a piezoelectric ceramic in an electrically-inactive polymer matrix. Combining the ceramic with polymer filler lowers an overall piezocomposite material density that provides a better match between the acoustic impedance of the device and that of water thus improving acoustic power transfer efficiency. The lateral coupling that typically occurs between different modes in large ceramic transducers is also reduced, thereby improving precision and predictability of ultrasound array transducers. Reduction in parasitic vibrations also offers a potential for miniaturization of piezocomposite transducers, which is critical in medical applications. The present invention aims in part to provide an ultrasonic transducer device wherein lateral coupling is reduced, parasitic surface waves are suppressed and there is a dual, therapeutic and diagnostic, mode of transducer operation. This is achieved, for instance, in a piezocomposite transducer of the present invention wherein piezoceramic elements are embedded in a PVDF polymer matrix, a piezoelectrically active polymer filler.

One can fabricate piezocomposite transducers of the present invention by cutting a ceramic material into small elements having a linear dimension or edge length comparable to the wavelength of the respective ultrasonic pressure waves in water while maintaining a width to thickness aspect ratio requirement to operate the transducers in a thickness mode. The sizes of the transducer elements are varied to suppress the additional resonances caused by interference of the lateral vibration modes. The area between ceramic elements is filled with urethane, epoxy resin or similar polymers. The filling material reduces overall acoustic impedance and makes it feasible to mold curved transducers. Adding low-durometer flexible polymer inclusions, for instance, of silicon rubber, can enable one portion of piezocomposite transducer to move relative to another portion of the transducer resulting in a change of the transducer shape by plastically deforming the inclusions. Such movement can be controlled by applying lateral movement to wedge-shaped spatial mounts by anchoring them to a flexible backing plate.

The present invention provides a new type of piezocomposite transducer having an interpenetrant structure of piezoceramic and piezoactive polymer PVDF. Such a transducer effectively functions as a dual mode therapy and imaging transducer. One of the strong advantages of this piezocomposite is the use of piezoceramic elements for therapy and piezoelectric polymer substrate for imaging. At the same time, the polymeric substrate improves the therapeutic efficiency of the ceramic elements by suppressing the parasitic surface mode vibrations otherwise present in large ceramic elements.

In the development of ultrasound transducers, the deposition of an acoustic matching layer on a face of a ceramic element is one of the most challenging manufacturing processes. By using polymeric piezoelements with acoustic impedance comparable to that of water, the need for an acoustic matching layer for imaging elements is essentially eliminated, which significantly reduces the cost of manufacturing. Moreover, using piezoactive PVDF as a filler material engages otherwise acoustically untapped interstitial space for good quality imaging and offers a potential for miniaturization of such transducers. For a variety of biomedical applications miniaturization can be achieved using flex-circuit, Which, like standard circuit boards, enables cost-effective fabrication of different electrode patterns and activation of piezocomposite transducer as a single element or an array. The PVDF polymer transducers combined with low durometer polymer, such as urethane, silicon, or flexible foam, has a potential to enable spatially distributed, movable transducers with, for example, variable transducer aperture and focal depth.

Preliminary experiments were conducted to verify the feasibility of dual mode therapy and imaging using single element ceramic-polymer assembly. A concave ceramic element having a focal length of 3.5 mm, encased in a tubular plastic housing having a diameter of 13 mm and about 30 mm in length was used. A disk of PVDF (diameter 8 mm, density 1.88 gm/cm$^3$, sound speed 2.28 mm/µs, resonance/anti-resonance frequency 4.9/14.9 MHz, capacitance 2.3 pF at 1 MHz) was attached to an electrically masked area on the larger surface focused ceramic element and acoustic imaging was tested. The ceramic element of the device had a resonance frequency in water of about 3.8 MHz and efficiency above 60%, while the imaging element showed a broad frequency response in water between 1 and 7 MHz. The two elements were connected in parallel. The device was able to deliver high power in a therapeutic mode at 3.8 MHz without damage or degradation of the PVDF imaging element. The imaging mode performance of device was tested using standard ballistic gel imaging phantom and found adequate.

Implicit registration between the imaging and therapy elements of a transducer device in accordance with the present invention ensures proper alignment between the therapeutic ultrasound beam and the planned treatment volume. In preliminary experiments, strong imaging pulses were produced by the high-power piezoceramic elements, while respective echoes were received by the sensitive polymeric element. Such an arrangement is applicable in the case of multiple therapy and imaging transducers with imaging signals processed in real-time to guide and monitor ablation treatment. In summary, a dual mode piezocomposite transducer as described herein is favorably characterized by an improved frequency bandwidth and reduction in parasitic vibrations, which improves performance of imaging elements for diagnostics, while maintaining high efficiency of therapeutic elements for treatment, also reducing the amount of passive materials and thus offering a potential for miniaturization and customization of the dual mode transducers for medical applications.

DETAILED DESCRIPTION

The present invention stems in part from an appreciation of the properties of polyvinylidene fluoride (PVDF), which is a semi-crystalline, thermoplastic fluoroplastic. It has received a considerable research attention in past decades after its piezoelectric and pyroelectric properties were discovered and it found a subsequent application as an electret and piezoelectric transducer. With its low acoustic impedance of 3.5 MRyals and high voltage constant PVDF makes an ideal ultrasound receiver and shows definite advantages over ceramic counterparts (Gallentree, 1983, Review of Transducer Applications of Polyvinylidene Fluoride, *Piezoelectricity*, Key Paper in Physics, 189-194). As a transmitter of acoustic power, the PVDF transducer is quite poor, its dielectric losses are quite high, but its enhanced sensitivity on reception provides a send-receive factor comparable to that of ceramic. Table below summarized common applications and lists relevant piezoelectric properties for typical piezoelectric ceramic, quartz and PVDF.

| | | Piezoelectric material properties | | | |
|---|---|---|---|---|---|
| | Applications | Curie T, ° C. | $Q_m$ | $d_{33}$, m/V $10^{-12}$ | $g_{33}$, Vm/N $10^{-3}$ |
| Navy Type I (PZT4) | STM, nanopositioning, medical therapeutics. | 328 | 500 | 289 | 25 |
| Navy Type II (PZT5A) | flow and level sensing and medical Doppler transducers | 365 | 75 | 374 | 25 |
| Navy Type III (PZT8) | Ultrasonic cleaners, cell disruption, phacoemulsification, and high power ultrasonics | 300 | 1000 | 225 | 25 |
| Navy Type VI (PZT5H) | Medical diagnostics, industrial NDT, STM/AFM, and nano-positioning | 193 | 65 | 593 | 20 |
| PVDF | Insulation (Kynar ®), key boards, sonar hydrophones, pulse-echo ultrasonic transducers | 100 | 13 | 20 | 210 |
| Quartz | Crystal clock oscillator, mass microbalance, and thin-film thickness monitoring | — | 25000 | 2 | 50 |

(Gallentree, 1983, Review of Transducer Applications of Polyvinylidene Fluoride, *Piezoelectricity*, Key Paper in Physics, 189-194; Kino, 1987, Acoustic Waves: Devices, Imaging, and Analog Signal Processing, Prentice Hall, Englewood Cliffs, NJ, Appendix B; Mason, 1966, Physical Acoustics: Principles and Methods, edit Rosenberg, Mir, Moscow.)

Needless to say that a combination of PVDF receiving signals with any high power ceramic producing test pulses constitutes a material that offers a unique set of properties yielding substantially higher send-receive factor than the standalone materials.

A typical PVDF transducer does not require cumbersome acoustic matching layers, inherent in high acoustic impedance ceramic imaging transducers, and PVDF is relatively easy to extrude or press fit into a variety of forms and shapes (Ketterling and Lizzi, 2005, Design and Fabrication of a 40-MHz Annular Array Transducer, IEEE, *Trans. Ultrason Ferroelectr. Freq. Control*, April; 52(4): 672-681).

Figure 1:
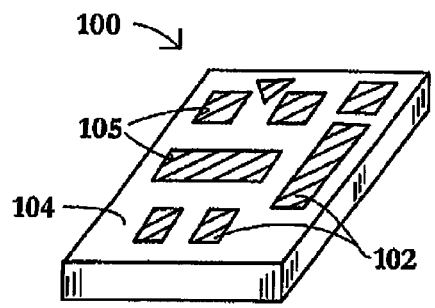
FIG. 1 is a schematic isometric view of a dual mode piezocomposite transducer in accordance with the present invention.

FIG. 1 depicts a dual mode piezocomposite transducer 100 comprising a plurality of hard ceramic transducer elements 102 embedded in a piezoelectric polymeric matrix 104. Transducer elements 102 are all spaced from one another by virtue of intervening portions of the polymeric matrix 104.

Piezoelectric polymeric matrix 104 may be a single continuous substrate provided with a plurality of recesses, grooves, holes, cuts, dimples, or indentations 105 filled with piezoelectric ceramic material to thereby form piezoelectric ceramic transducer elements 102.

Ceramic transducer elements 102 function in a therapy mode of operation of transducer 100 to generate high-power ultrasonic pressure waves, in response to a suitable energizing signal, that are transmitted into a patient for implementing or assisting in surgical operation such as thermal ablation, hyperthermia, transfection and/or drug delivery. Polymeric matrix 104 serves as a diagnostic transducer element for detecting incoming ultrasonic pressure waves that are reflected and scatter from internal tissue structures of a patient in response to a suitable scanning wave. As discussed hereinafter with reference to FIG. 11, therapeutic ceramic transducer elements 102 and diagnostic polymeric transducer element 104 may be connected in parallel in the same circuit.

Polymeric piezoelectric materials suitable for diagnostic transducer element 104 include polyvinylidene fluoride (PVDF), and copolymers of PVDF such as trifluoroethylene (TrFE) with a piezoelectric voltage constant $g_{33} > 100 \times 10^{-3}$ Vm/N. Piezoceramic materials suitable for therapeutic transducer elements 12 include modifications of $BaTiO_3$, $Pb(Ti,Zr)O_3$ (PZT) and $PbNb_2O_6$ ceramics with a high piezoelectric strain constant, $d_{33} > 200 \times 10^{-12}$ m/V. These materials are also utilizable in other embodiments of a piezocomposite transducer device discussed hereinafter.

Piezocomposite transducer 100 offers several advantages over single crystal transducer designs (see U.S. Pat. No. 5,117,832 to Sanghvi et al., 1992), multi-layer transducer designs (U.S. Pat. No. 6,492,762 to Pant et al., 2002) and spatially distributed transducer designs (see U.S. Pat. No. 6,461,314 to Pant et al., 2002). These advantages include an enhanced therapeutic efficiency, a broad bandwidth and high sensitivity in the imaging mode, an ability to work in dual mode—therapy and imaging, potential for miniaturization, cost reduction, improved manufacturability, and ability to make flexible transducer (Safari, 1992, Flexible Composite Transducers, *J. Am. Ceram. Soc.*, 65: 207-209).

Figure 2:
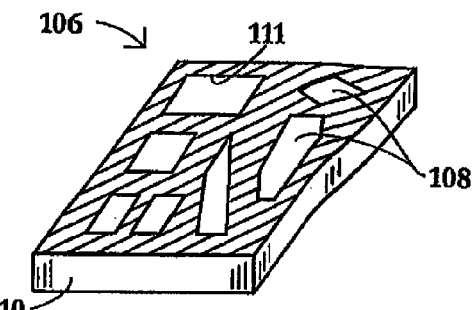
FIG. 2 is a schematic isometric view of another dual mode piezocomposite transducer in accordance with the present invention.

FIG. 2 depicts a dual mode piezocomposite transducer 106 comprising a plurality of piezoelectric polymeric transducer elements 108 embedded in a hard ceramic matrix 110. Transducer elements 108 are all spaced from one another by virtue of intervening portions of the ceramic matrix 110.

Ceramic matrix 110 may be a single continuous substrate provided with a plurality of recesses, grooves, holes, cuts, dimples, or indentations 111 filled with piezoelectric polymeric material to thereby form polymeric transducer elements 108.

Polymeric transducer elements 108 serve as diagnostic transducer elements for detecting incoming ultrasonic pressure waves that are reflected from internal tissue structures of a patient in response to a suitable scanning wave. Ceramic matrix 110 functions as a therapeutic transducer element that generates high-power ultrasonic pressure waves, in response to a suitable energizing signal, that are transmitted into a patient for implementing or assisting in a surgical operation such as thermal ablation, hyperthermia, transfection and/or drug delivery. As indicated above with reference to FIG. 1 and as discussed hereinafter with reference to FIG. 11, diagnostic polymeric transducer elements 108 and therapeutic ceramic transducer element 110 may be connected in parallel in the same circuit.

Figure 3:
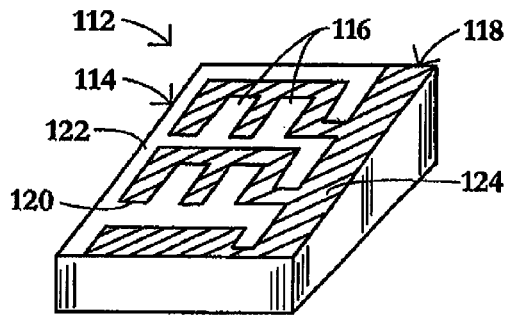
FIG. 3 is a schematic isometric view of a further dual mode piezocomposite transducer in accordance with the present invention.

As depicted in FIG. 3, a piezocomposite ultrasound transducer 112 comprises an imaging transducer element 114 including a plurality of first finger parts 116, while a therapeutic transducer element 118 includes a plurality of second finger parts 120. Finger parts 116 of imaging transducer element 114 and finger parts 120 of therapy transducer element 118 are interdigitated or interleaved with one another so that each transducer element is partially embedded in the other. Imaging finger parts 116 are all partially spaced from each other by one or more therapy finger parts 120. Concomitantly, therapy finger parts 120 are all partially spaced from each other by one or more imaging finger parts 116. Imaging finger parts 116 are joined to one another at a bight or hand portion 122 of imaging transducer element 114, while therapy finger parts 120 are joined to one another at a bight or hand portion 124 of therapeutic transducer element 118.

Several types of standard piezocomposites currently exist. Parallel oriented piezoceramic rods embedded in a bonding polymer matrix constitute the so-called 1-3 type architecture, typically manufactured by the dice and fill technique. Alternatively, the so-called 2-2 architecture includes alternating two-dimensional strips of piezoceramic and polymer disposed side by side, while the so-called 0-3 architecture includes a piezoelectric powder embedded in a polymer matrix. Imaging finger parts 116 can be arranged in form and shape to produce standard piezocomposite architectures. The volume fraction of piezoceramic can be tailored for any application to enhance transmit, receive, or transmit and receive response rates. The piezocomposite can be extruded or thermoformed to conform to curved, complex geometric surfaces to which conventional piezoceramic materials often cannot be shaped.

Transducer elements 114 and 118 are made of the materials described above and may be connected in a parallel circuit. In transducers 100, 106 and 112, imaging transducer elements 104, 108 and 114 may be activated independently of therapy transducer elements 102, 110 and 118, respectively, in diagnostic and therapeutic modes of operation.

Transducers 100, 106 and 112 offer lower mechanical impedance and better sensitivity due to lower impedance contrast with water and soft organic tissues, lower vibration losses due to parasitic resonances.

Figure 4:
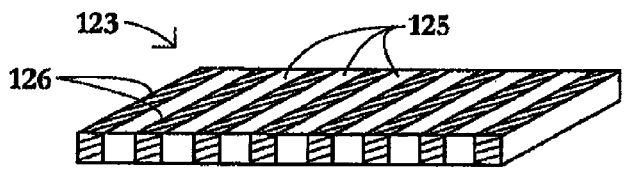
FIG. 4 is a schematic isometric view of a flexible dual mode piezocomposite transducer in accordance with the present invention, showing the transducer in a planar configuration.
Figure 5:
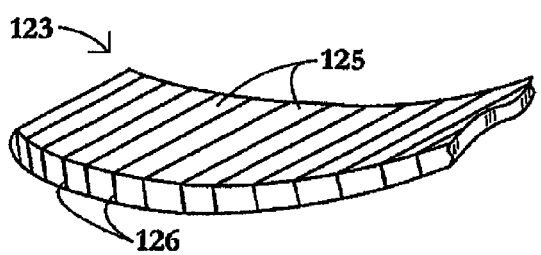
FIG. 5 is a schematic isometric view of the transducer of FIG. 4, showing the transducer in a flexed configuration for dynamic focusing.

As illustrated in FIG. 4, a piezocomposite ultrasound transducer device 123 comprises a plurality of imaging transducer elements 125 made of a piezoelectric polymeric material (discussed above) and a plurality of therapeutic transducer elements 126 made of piezoelectric ceramic material (discussed above). Polymeric transducer elements 125 and ceramic transducer elements 126 are elongate strips that are bonded to one another in alternating fashion so that each polymeric transducer element 125 is spaced from the other polymeric transducer elements by one or more ceramic transducer elements 126 and, correspondingly, so that each ceramic transducer element 126 is spaced from other ceramic transducer elements by one or more piezoelectric polymeric transducer elements 125. The regions of the polymeric transducer elements 125 may be provided with inserts of other polymeric material that enhances the flexibility of the polymeric regions, so that transducer device 123 may be deformed into a cylindrically focused concave configuration, as shown in FIG. 5, of variable curvature, thereby providing a range of focal lengths whereby tissue at different depths from an organ surface, or different distances from transducer 123 may be targeted.

Figure 6:
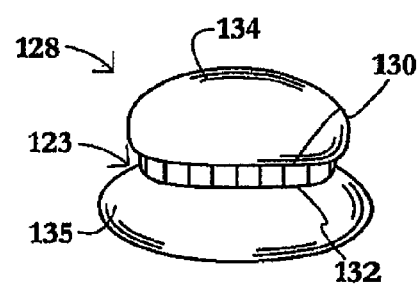
FIG. 6 is a schematic side elevational view of the transducer of FIGS. 4 and 5, showing bladder elements for implementing a flexing of the transducer.

FIG. 6 shows a structure 128 for exerting differential mechanical force on opposing major faces 130 and 132 of transducer element 123 to control deformation thereof into a parabolic or approximately cylindrical shape of variable curvature that has a linear focal locus, i.e., an elongate focal zone extending along a line. Structure 128 includes a first bladder 134 disposed in wave-transmitting contact with face 130 and filled with a liquid such as a saline solution and further includes a second bladder 135 disposed in contact against face 132 and filled with a gas such as air or carbon dioxide. The gas in bladder 136 serves to reflect pressure waves of an ultrasonic frequency, wile the liquid in bladder 134 transmits ultrasonic pressure waves.

Figure 7:
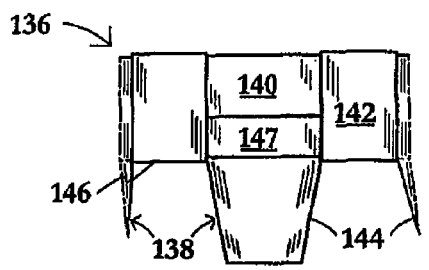
FIG. 7 is a schematic side elevational view of an additional dual mode piezocomposite transducer in accordance with the present invention, showing the transducer in a planar configuration.
Figure 8:
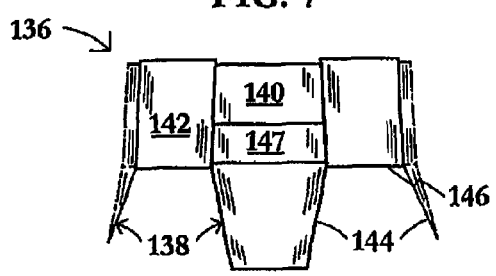
FIG. 8 is a schematic side elevational view of FIG. 7, showing the transducer in a flexed configuration for dynamic focusing.

FIGS. 7 and 8 depict a piezocomposite ultrasound transducer device 136 with an alternative structure 138 for flexing the transducer from a planar configuration (FIG. 7) into a an arcuate focusing configuration (FIG. 8). Transducer device 136 includes a plurality of imaging transducer elements 140 made of a piezoelectric polymeric material (discussed above) and a plurality of therapeutic transducer elements 142 made of piezoelectric ceramic material (discussed above). Polymeric transducer elements 140 and ceramic transducer elements 142 may be elongate strips that are bonded to one another in alternating fashion. Alternatively, polymeric transducer elements 140 and ceramic transducer elements 142 may be square elements that are bonded to one another in checkerboard fashion. In either case, each polymeric transducer element 140 is spaced from the other polymeric transducer elements by one or more ceramic transducer elements 142 and, correspondingly, each ceramic transducer element 142 is spaced from other ceramic transducer elements by one or more piezoelectric polymeric transducer elements 140.

Flexing structure 138 includes a plurality of mounting members 144 that are in contact with one major face 146 of transducer 136, particularly with a bonding substrate or layer 147, and that are spaced from one another. Spatial mounting members 144 are differentially movable in a direction perpendicular to transducer face 146 so as to deform the transducer 136 into either a cylindrically focused concave configuration or a spherically focused concave configuration of variable curvature and concomitantly variable focal length.

Figure 9:
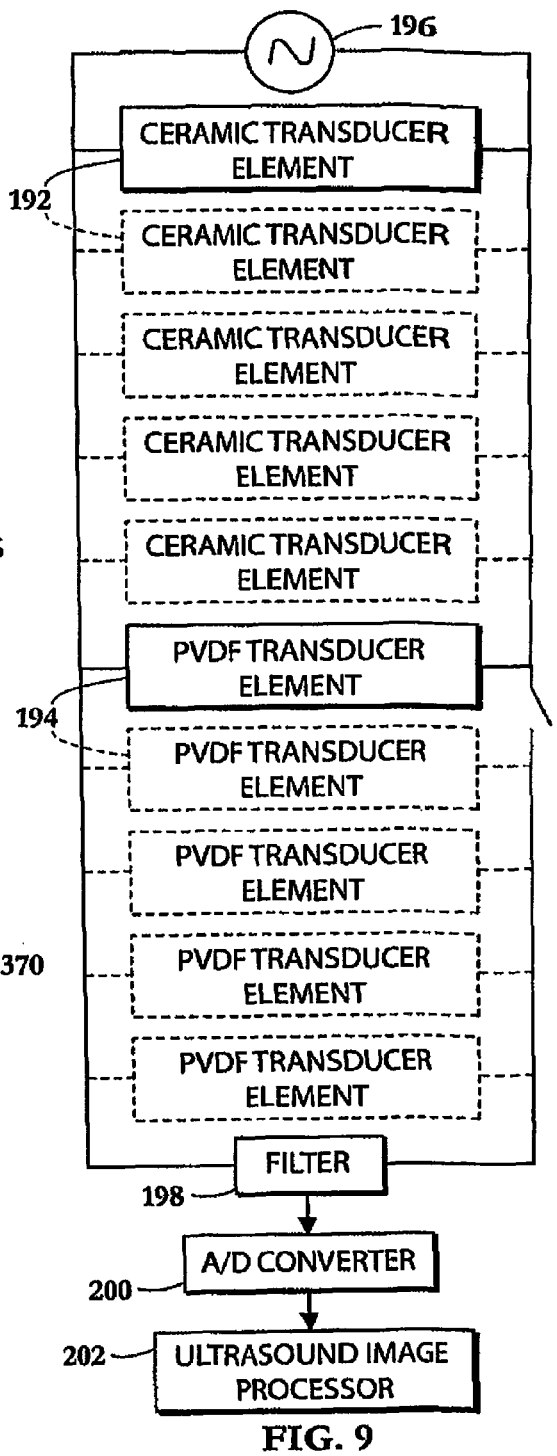
FIG. 9 is a circuit diagram incorporating a dual mode transducer, in accordance with the present invention.

FIG. 9 is a circuit diagram applicable to any of the dual mode piezocomposite transducers described herein. As shown in FIG. 9, one or more piezoelectric ceramic transducer elements 192 and one or more piezoelectric PVDF transducer elements 194 are connected in parallel to a source of high-intensity alternating voltage 196 and to a directional filter 198 having an output extending to an analog-to-digital converter 200 and from thence to an ultrasonic signal processor 202.

A relatively low driving voltage applied by source 196 to ceramic transducer elements 192 in a therapy mode does not engage PVDF transducer elements 194. PVDF transducer elements 194 have a substantially higher electrical impedance than the impedance of ceramic transducer elements 192 so that the total electrical impedance of the parallel circuit of FIG. 9 quite similar to that of ceramic, so that the presence of PVDF elements 194 in the circuit consequently has little effect on electrical power transfer and produced acoustic power. In an imaging mode, the low acoustic impedance of the PVDF transducer elements 194 provide larger amplitude broad band electrical signals to the ultrasound image processor 202 in response to received acoustic echoes due to the higher sensitivity of PVDF material relative to ceramic. The ceramic transducer elements 192 reflect most of the incoming acoustic energy due to high contrast in mechanical impedances between the ceramic and water in an absence of acoustic matching layers and produce much lower amplitude narrow band electric signals owing to the high power ceramic having a piezoelectric voltage constant that is an order-of-magnitude lower.

Ceramic transducer elements 192 and polymeric transducer elements 194 can share the same electrodes or be connected to different electrodes. The number of individual therapeutic ceramic transducer elements 192 and imaging polymeric elements transducer elements 194 depends on the application.

If a PVDF transducer element 194 is used to send and receive acoustic signals as it is done in a standard pulse-echo imaging systems, then there is a need to couple that PVDF transducer to both a high-voltage excitation pulse generator (not separately shown) and the sensitive receiving electronics, i.e., ultrasonic signal processor 202. A transmit-receive (T/R) switching circuit (not shown) that would close during the application of a higher voltage signal but open while the probe is receiving acoustic echoes can be used. Alternatively, one may use a circuit designed to send acoustic signals using one or more piezoceramic transducer elements 192 and receive echoes with PVDF transducer elements 194. This is feasible, because of close packed interpenetrant nature of piezocomposite transducers disclosed herein and consequent negligible differences in beam directivity between ceramic and polymer elements.

Piezocomposite ultrasound transducer devices 100, 106, 112, 123, and 136 are provided with electrical contacts (not shown) enabling a connection of the respective ceramic transducer elements 102, 110, 118, 136, 142, and 368 in operative circuits for generating, for example, high-intensity focused ultrasound and enabling a connection of the respective polymeric transducer elements 104, 108, 114, 125, 140, 212, and 370 in operative circuits for scanning organic tissues to generate ultrasonic scan data for analysis and processing into images. Piezocomposite ultrasound transducer devices 100, 106, 112, 123, and 136 may be further provided with mounting elements (not shown) for mechanically coupling the transducers exemplarily inside a probe or housing (not shown) and more particularly inside a liquid-filled bolus (not shown) that is contactable with a tissue surface to enable ultrasonic wave transmissions into and from organic tissues of a patient. Focusing lenses exemplarily in the form of acoustic Fresnel lenses (not shown) may be provided as necessary, particularly for piezocomposite ultrasound transducer devices 100, 106, and 112.

Dual-mode piezocomposite transducer devices 100, 123, 136, and 364 may be activated by an alternative circuit configuration in which piezoelectric ceramic transducer elements 102, 126, 142, and 368 of the respective transducer devices are electrically independent from each other with at least a subset of the transducer elements being operable as a phased array while cross talk between members of the subset is minimized. Likewise, piezoelectric polymeric transducer elements 108, 125, 140, and 370 of transducer devices 100, 123, 136, and 364 may be activated (energized and/or poled) by an alternative circuit configuration in which the piezoelectric polymeric transducer elements 108, 125, 140, and 370 are electrically independent from each other with at least a subset of the transducer elements being operable as a phased array while cross talk between members of the subset is minimized.

Figure 12:
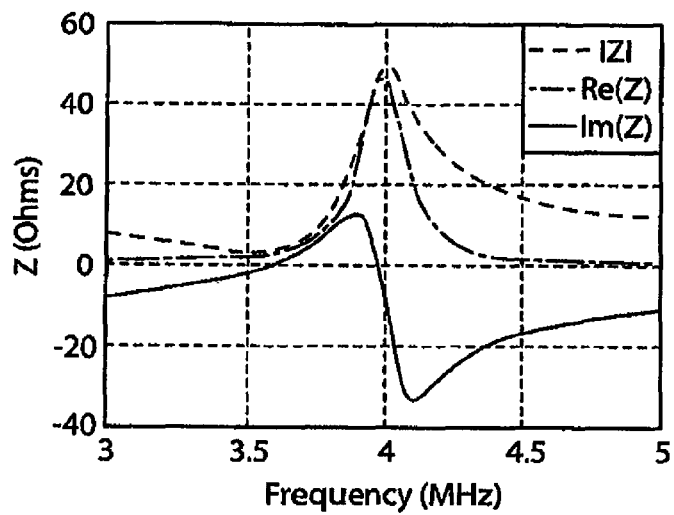
FIG. 12 is a graph of impedance as a function of frequency for ceramic (PZT) materials.
Figure 13:
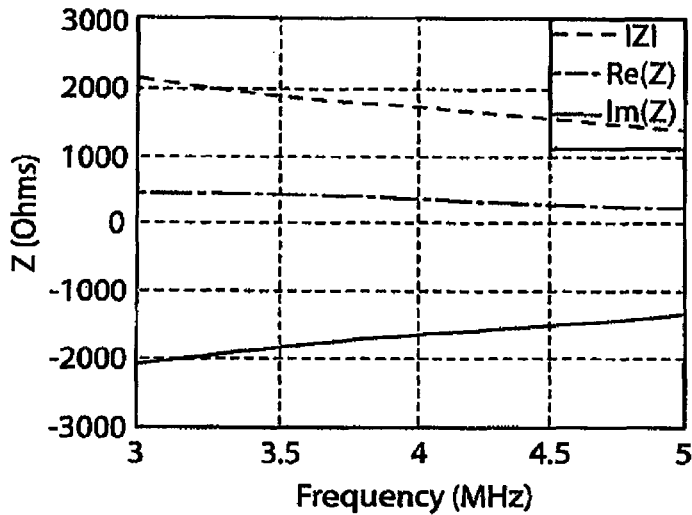
FIG. 13 is a graph of impedance as a function of frequency for polymeric (PVDF) materials.

Electro-acoustic performance of a piezoelectric element with a given laminate structure and materials can be simulated using the KLM model. (Krimholtz, Leedom, Matthaie 1970, New Equivalent Circuits for Elementary Piezoelectric Transducers, *Electron Lett,* 6, 13, 398-399.) This model can also be used to predict heat production and electrical power requirements. For example, calculated electrical impedance of 2 $cm^2$ PZT Navy Class III element is resistive at 4 MHz resonance and presents a good electrical match to a 50 Ohms output impedance system. An electrical impedance of an equidimensional PVDF element is almost purely reactive and it is two orders of magnitude large in absolute value. The electrical impedance curves for ceramic (PZT) and polymeric (PVDF) elements are shown in FIGS. 12 and 13.

Consistent with basic theory and development experience of therapeutic PVDF phased arrays, the large reactive electrical impedance of PVDF requires a significant driver voltage of 1000 Volts peak-to-peak to achieve 3-5 W/cm² acoustic power output. The same output acoustic power can be achieved in a ceramic driver only with 50 Volts peak-to-peak. Producing such and excessive drive voltage is technologically difficult, limiting the application of PVDF to a low power imaging applications.

Figure 10:
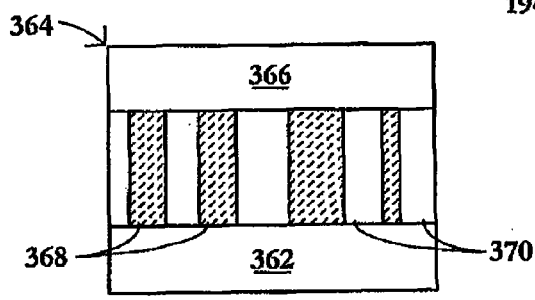
FIG. 10 is a schematic side elevational view of a flexible piezocomposite ultrasound transducer in accordance with the present invention.

One method of construction a piezocomposite transducer or array made of ceramic and polymeric elements will now be described. The idea is to encapsulate the piezocomposite transducer made of a mix of ceramic and PVDF elements and flexible filler material between front and rear flex circuit layers. Ceramic elements provide high-intensity ultrasound in a therapeutic operating mode. The PVDF elements are used exclusively for imaging while ceramic elements are used predominantly for therapy and to produce high power acoustic imaging pulses. In a piezocomposite design, parasitic surface vibrations are dampened, leading to an improved therapeutic efficiency. Intramural area consumed by PVDF enables good-sensitivity medical imaging using a single or multiple elements and provides the potential for overall miniaturization of the piezocomposite design. A shunt inductor of the value $1/(\omega_0^2 C_0)$, where $\omega_0$ is the radial frequency, capacitance $C_0 = \in^s A/t$, $\in^s$ is the clamped dielectric constant, A is the area of PVDF and t is the thickness, can be used to tune out the reactive component of PVDF elements. As shown in FIG. 10, each of the piezocomposite transducer devices described herein may have a final structure comprising a front flex-circuit layer 362, a piezocomposite layer 364 and a rear flex-circuit layer 366. Front electrode layer 362 consists of a piece of polyimide (Kapton®) flex-circuit with a single copper plane. This plane serves as the ground plane for the entire device, including ceramic and imaging elements. Piezocomposite layer 364 consists of individual ceramic and polymeric elements 368 and 370, which may be diced from one or several flat, poled, and plated pieces of PZT and PVDF. These elements 368 and 370 are bonded together with an adhesive to form a solid layer. Alternatively, ceramic elements 368 can be hot pressed into a polymeric PVDF substrate followed by subsequent poling. Rear flex-circuit layer 366 consists of a four-layer flex circuit (1) hot electrode pads for each element; (2) a ground plane (to minimize electrical coupling between elements); (3) a route layer (to route the individual signal lines to the edge of the array for contacts); and (4) a ground plane (for RF shielding and reduction of electrical coupling between elements).

A piezocomposite transducer with an arbitrary number of therapy and imaging transducers may be constructed in a flat or concave shape as follows.

In outlined construction method one, first, forms a piezocomposite layer 364 by hot pressing ceramic elements arranged in a desired geometrical pattern into a polymeric substrate at an elevated temperature not exceeding the Curie temperature of ceramic. Second, one immerses the hot-pressed piezocomposite layer 364 into an oil at about 100° C. and subjects it to an electric field of about 80 MV/m via external surface electrodes in order to produce or restore desired ferroelectric activity in a PVDF film surrounding ceramic elements 368. The polarization of ceramic elements is not substantially affected below its Curie temperature, which is around 300° C.-350° C. for a typical high power ceramic. Next, one laminates the front flex-circuit layer 362 onto the cooled piezocomposite layer 364 using a low viscosity epoxy adhesive. The electrical contacts can also be established by bonding thin wires with a conductive epoxy, sputtering process, electrolytic deposition. Optionally, using a conventional acid bath and solvent sequence, one etches a thickness of PVDF away to fill it with low-durometer polymer and obtain a spatially distributed, movable design. Additionally, the etched voids can be filled with metal powder to improve the longevity and thermal performance of piezocomposite in therapeutic high power mode. This process can also be performed using a precision milling machine or dicing saw to produce grooves in a piezoactive polymeric substrate that can later be filled with flexible passive polymer. A non-piezoelectric polymer (Kynar®) can also be press-bonded to the back of imaging elements in order to obtain a fundamental thickness resonance in PVDF of a half wavelength. Next, one heats the array slightly and wicks in an epoxy adhesive between the elements. This is a standard technique for making imaging arrays. Finally, one laminates the rear flex-circuit 366 onto the back of the piezocomposite layer 264. A similar process can be used when starting with a solid piece of piezoceramic and creating a plurality of recesses, grooves, holes, cuts, dimples, or indentations on its surface that are later filled with polymeric material, which is later poled to thereby form a piezocomposite transducer element.

Figure 11:
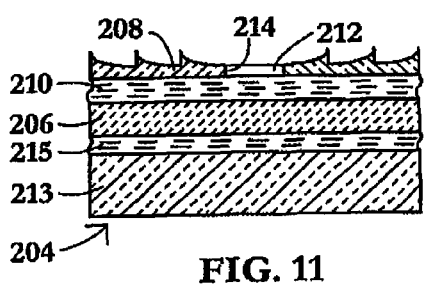
FIG. 11 is a schematic cross-sectional view of a dual mode transducer assembly in accordance with the present invention.

FIG. 11 depicts a dual mode transducer assembly 204 including a piezoceramic therapy transducer element 206 and an acoustic Fresnel lens 208 spaced from one another by a liquid layer 210. Fresnel lens 208 is provided in a central region with a piezoelectric polymeric imaging transducer element 212. Transducer element 212 occupies a through hole 214 in the lens. A backing layer 213 is paced by a liquid layer 215 from a back side of ceramic transducer element 206.

The volume fraction of piezoceramic to polymeric transducers may be tailored for a particular application need to enhance transmit, receive, or transmit and receive response rates, and the volume fraction is not uniform across a surface of a dual-mode piezocomposite transducer device as disclosed herein.

The calculated electrical impedances of Navy Class III piezoceramic and PVDF piezopolymeric transducers with a surface area of 2 cm² are shown in FIGS. 12 and 13 respectively, and are provided herein to illustrate significant differences in the electro-mechanical material properties of dual mode piezocomposite transducer constituents.

Figure 14:
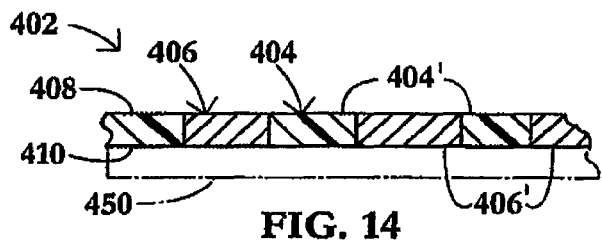
FIG. 14 is a schematic cross-sectional view of a dual-mode piezocomposite transducer module or element in accordance with the present invention.

As illustrated in FIG. 14, a dual-mode piezocomposite transducer module or device 402 as described hereinabove with reference to FIGS. 1-4 and 10 may comprise at least one piezoelectric polymeric imaging transducer element 404 and at least one piezoelectric ceramic therapy transducer element 406 that include interleaved sections 404' and 406', respectively arranged in a planar array. Each transducer section or separate transducer element 404' and 406' extends from one face 408 of the dual-mode piezocomposite transducer module through to an opposite face 410 thereof.

Figure 15:
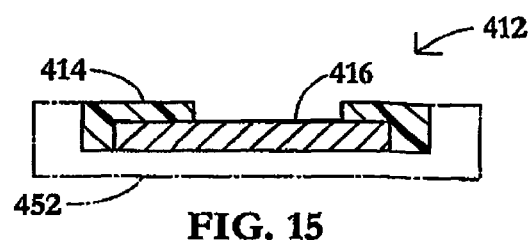
FIG. 15 is a schematic cross-sectional view of another dual-mode piezocomposite transducer module or element in accordance with the present invention.

As depicted in FIG. 15, a dual-mode piezocomposite transducer module or device 412 as described hereinabove with reference to FIGS. 1-4 and 10 may comprise at least one piezoelectric polymeric imaging transducer element 414 and at least one piezoelectric ceramic therapy transducer element 416 arranged in an overlapping array.

Figure 16:
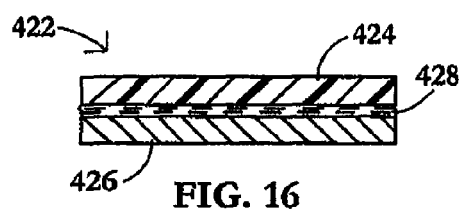
FIG. 16 is a schematic cross-sectional view of a further dual-mode piezocomposite transducer module or element in accordance with the present invention.

As shown in FIG. 16, a dual-mode piezocomposite transducer module or device 422 as described hereinabove with reference to FIGS. 1-4 and 10 may comprise at least one piezoelectric polymeric imaging transducer element 424 and at least one piezoelectric ceramic therapy transducer element 426 that are stacked one over the other, with the piezoelectric polymeric imaging transducer element 424 disposed on the transmitting side of the piezoelectric ceramic therapy transducer element 426, that is, between the piezoelectric ceramic therapy transducer element 426 and the target tissue. Transducer elements 424 and 426 may be mounted in a holder so as to be spaced by a layer 428 of water or other liquid.

Figure 17:
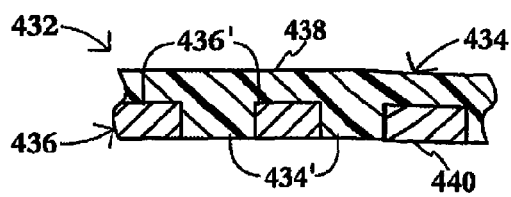
FIG. 17 is a schematic cross-sectional view of yet another dual-mode piezocomposite transducer module or element in accordance with the present invention.

As represented in FIG. 17, a dual-mode piezocomposite transducer module or device 432 as described hereinabove with reference to FIGS. 1-4 and 10 may comprise at least one piezoelectric polymeric imaging transducer element 434 and at least one piezoelectric ceramic therapy transducer element 436 that include interleaved sections 434' and 436', respectively arranged in a planar array. Polymeric transducer element 434 extends from a front face 438 of the dual-mode piezocomposite transducer module 432 through to a back face 440 thereof. Ceramic transducer sections or individual elements 436' are disposed in recesses, grooves, cuts, notches or indentations 442 and extend from back face 440 only partway toward front face 438.

Where modules 402, 412, 422, and 432 have multiple separate piezoelectric polymeric transducer elements 404', 414, 424, 434', those elements are electrically independent from each other and at least a subset of piezoelectric polymeric transducer elements 404', 414, 424, 434' may be operated as a receiving array (e.g., as a phased array) while acoustical and electrical cross talk between members of the subset is minimized. To that end each polymeric transducer element 404', 414, 424, 434' is provided with a pair of electrodes (not shown) separately connectable to an ultrasound signal processor 202 (FIG. 9).

Where modules 402, 412, 422, and 432 have multiple separate piezoelectric ceramic transducer elements 406', 416, 426, 436', those elements are electrically independent from each other and at least a subset of piezoelectric ceramic transducer elements 406', 416, 426, 436' may be operated as a phased array, while acoustical and electrical cross talk between members of the subset is minimized. Each ceramic transducer element 406', 416, 426, 436' is provided with a pair of electrodes (not shown) separately connectable to an ultrasonic-frequency waveform generator or voltage source 196 (FIG. 9).

The imaging and therapy elements of a dual-mode piezocomposite transducer device as disclosed herein may be mechanically held together by means of an open cell metallic foam structure that permits water flow and efficient cooling and characterized by good electrical conductivity. Such a foam structure is depicted schematically at 450 and 452 in FIGS. 14 and 15.

Figure 18:
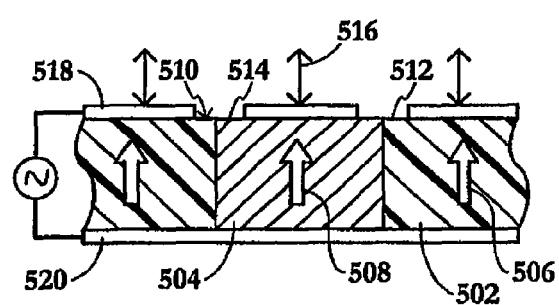
FIG. 18 is a schematic partial cross-sectional view of a dual-mode piezocomposite transducer module or element in accordance with the present invention, showing a poling scheme.

FIG. 18 shows a portion of a dual mode piezocomposite transducer module having polymeric imaging elements 502 and ceramic therapy elements 504 that are both poled, as indicated by arrows 506 and 508, in a direction normal to a surface 510 comprising individual emitting and receiving element surfaces 512 and 514. Double headed arrows 516 indicate the direction of vibration, that is, the direction along which alternating compression and rarefaction occur, while reference numerals 518 and 520 designate electrodes.

Figure 19:
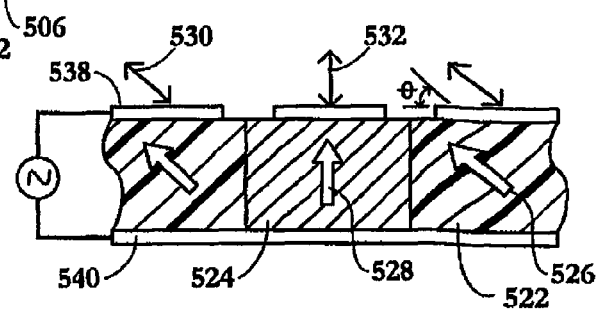
FIG. 19 is a schematic partial cross-sectional view of a dual-mode piezocomposite transducer module or element, similar to FIG. 18, showing another poling scheme.

FIG. 19 shows a portion of a dual mode piezocomposite transducer module having polymeric imaging elements 522 and ceramic therapy elements 524 that are poled, as indicated by arrows 526 and 528, in different directions to enable a simultaneous emission and reception of substantially different ultrasonic waves 530 and 532 to simultaneously monitor and induce lesion formation. Ultrasonic waves 530 and 532 are represented by double headed arrows that indicate the different directions of vibration, while reference numerals 538 and 540 designate electrodes.

Figure 20:
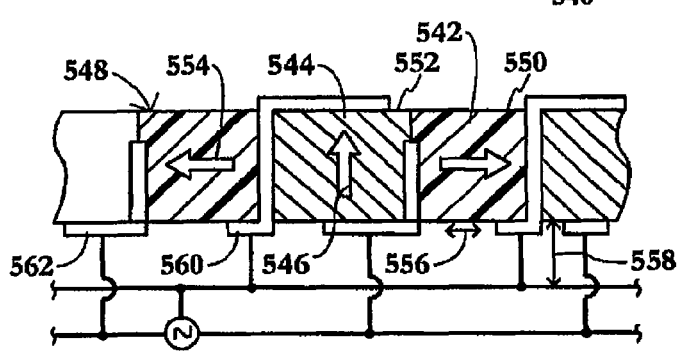
FIG. 20 is a schematic partial cross-sectional view of a dual-mode piezocomposite transducer module or element, similar to FIGS. 18 and 19, showing a further poling scheme.

FIG. 20 shows a portion of a dual mode piezocomposite transducer module having polymeric imaging elements 542 and ceramic therapy elements 544 wherein the latter, as indicated by arrow 546, is poled in the thickness mode normal to a surface 548 comprising individual emitting and receiving elements surfaces 550 and 552. Piezoelectric polymeric elements 542 are poled, as indicated by arrows 554, in a perpendicular direction radial to the center of said device in order to maximize the ability to perform multiwave imaging. Double headed arrows 556 and 558 indicate the different directions of vibration, while reference numerals 560 and 562 designate electrodes.

Figure 21:
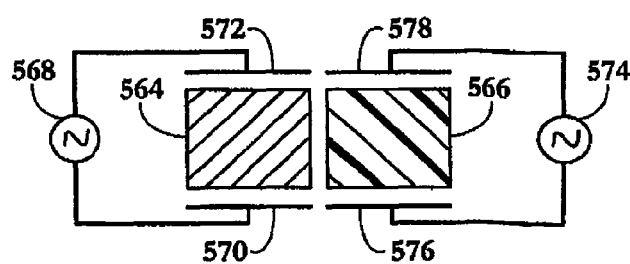
FIGS. 21-23 are schematic partial cross-sectional views of a dual-mode piezocomposite transducer module, in a parallel or planar array, showing different electrode configurations.

FIG. 21 depicts a dual-mode piezocomposite transducer device comprising multiple ceramic transducer elements 564 (only one shown) and multiple polymeric transducer elements 566 (only one shown) that are disposed in a laterally alternating or interleaved arrangement in a plane. Ceramic transducer elements 564 are energized by alternating voltage from a source 568 that is connected to the ceramic transducer elements via one or more ground electrodes 570 and one or more principal electrodes 572. Likewise, one or more polymeric transducer elements 566 may be energized by alternating voltage from a source 574 that is connected to the polymeric transducer elements via one or more ground electrodes 576 and one or more principal electrodes 578. In addition, polymeric transducer elements 566 are scanned or sampled by an ultrasound imaging circuit (see FIG. 9).

Figure 22:
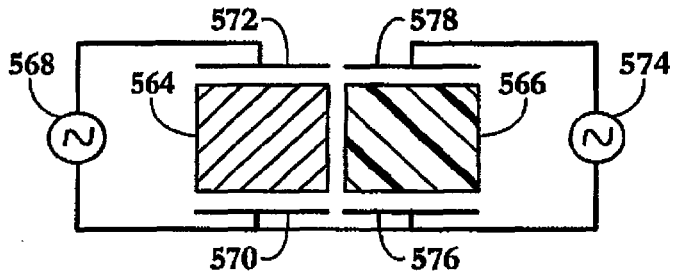

FIG. 22 depicts a transducer device and circuit similar to that of FIG. 21, except that the ground electrodes 570 and 576 of the ceramic transducer elements 564 and the polymeric transducer elements 566 are commonly grounded.

Figure 23:
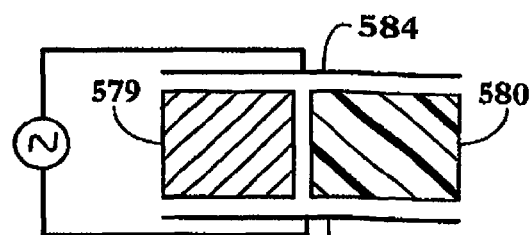

As illustrated in FIG. 23, a dual-mode piezocomposite transducer device comprising planar array of interleaved ceramic transducer elements 579 (only one shown) and polymeric transducer elements 580 has a common ground electrode 582 and a common main electrode 584. This configuration is discussed above with reference to FIG. 9.

FIGS. 24-29 illustrate different electrode arrangements for a dual mode piezocomposite transducer device wherein recesses, grooves, holes, cuts, dimples, or indentations 586 in a piezoelectric ceramic transducer matrix or base 588 are filled with piezoelectric polymeric material to form a plurality of imaging elements 590. The same electrode arrangements may be used in the reverse configurations (not shown) where the recesses, grooves, holes, cuts, dimples, or indentations 586 in provided in a polymeric transducer element matrix and are filled with piezoelectric ceramic material to form a plurality of therapy elements.

Figure 24:
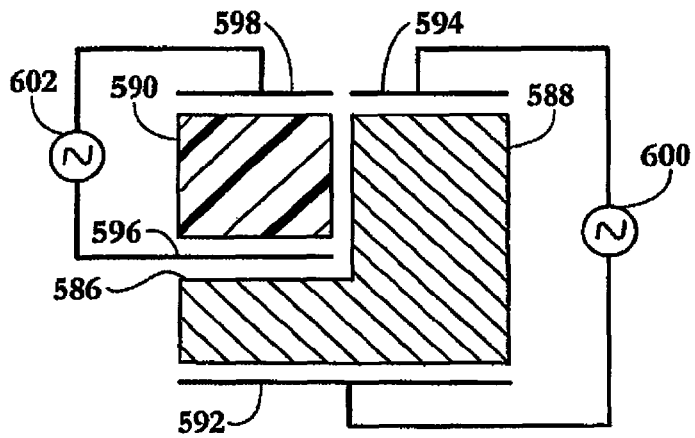
FIGS. 24-29 are schematic partial cross-sectional views of a dual-mode piezocomposite transducer module, in a cut-and-groove array, showing different electrode configurations.

In FIG. 24, piezoelectric ceramic transducer element(s) 588 have ground electrodes 592 and principal electrodes 594, while piezoelectric polymeric transducer elements 590 have separate ground electrodes 596 and principal electrodes 598. Ceramic element electrodes 592 and 594 are connectable to a source 600 of waveform energy, while polymeric element electrodes 596 and 598 are connectable to an ultrasound imaging circuit (see FIG. 9) and/or source 602 of waveform energy.

Figure 25:
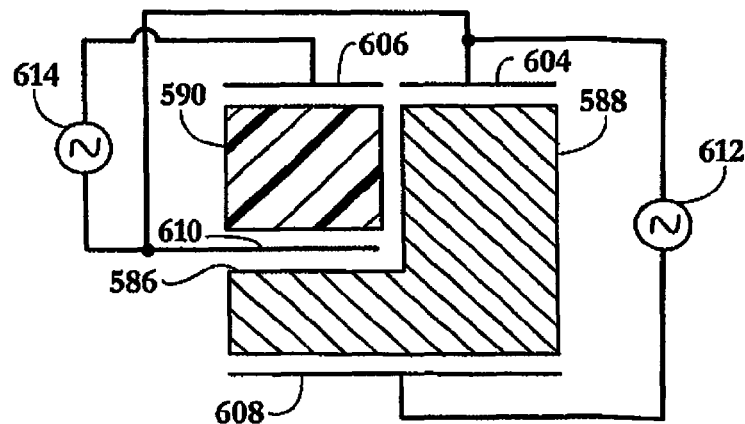

In FIG. 25, ceramic transducer element(s) 588 and polymeric transducer elements 590 have ground electrodes 604 and 606 that are interconnected and respective principal electrodes 608 and 610 that are electrically isolated by respective voltage sources 612 and 614 or signal sampling and processing circuits (in the case of the imaging elements 590).

Figure 26:
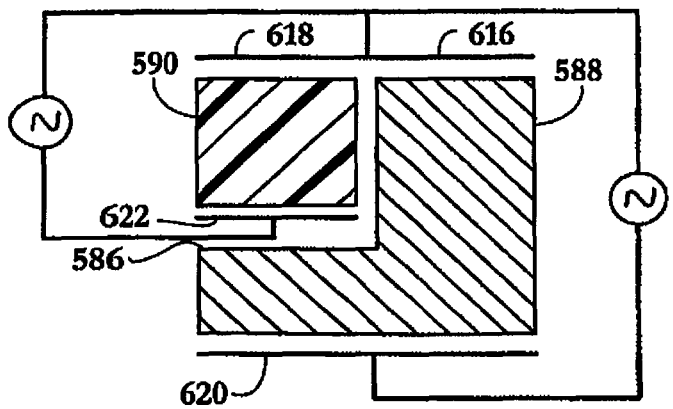
Figure 27:
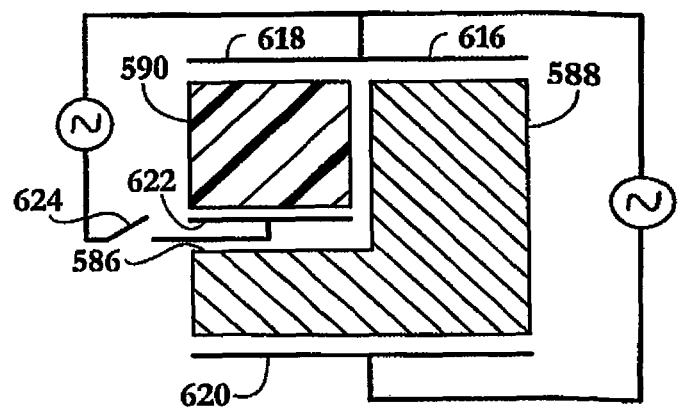

FIG. 26 shows a different electrode arrangement wherein ground electrodes 616 and 618 are interconnected and main electrodes 620 and 622 are separate. FIG. 27 is the same as FIG. 26 except for the inclusion of a switch 624.

Figure 28:
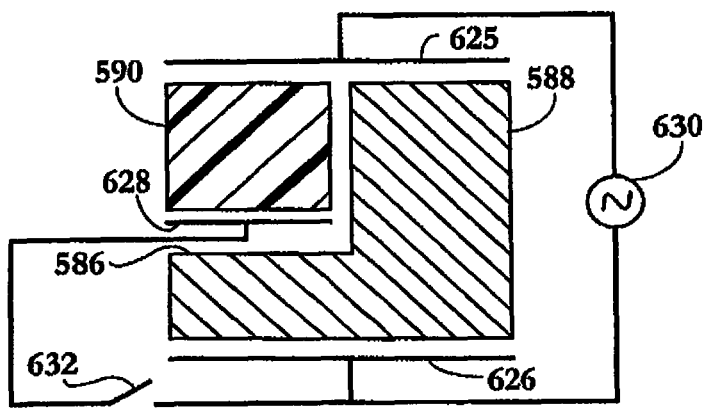

FIG. 28 depicts an electrode configuration including a common ground electrode 625 and separate main electrodes 626 and 628 alternately energizable by a common power supply 630 through the operation of a switch 632.

Figure 29:
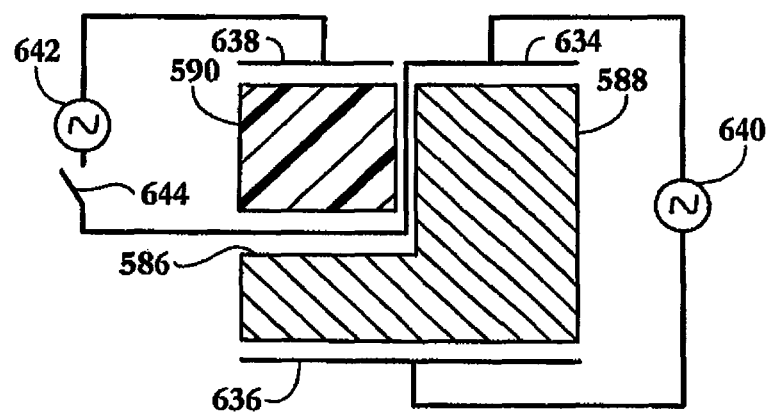

FIG. 29 illustrates an electrode configuration including a common ground electrode 634 and separate main electrodes 636 and 638 energizable by respective power supplies 640 and 642 (or poled by sampling and processing circuitry, in the case of polymeric imaging transducers 590). A switch 644 deactivates the polymeric imaging transducers 590.

The invention claimed is:

1. An ultrasonic transducer device comprising a plurality of first transducer elements all of a first type and at least one second transducer element of a second type different from said first type, said first type being one of an imaging transducer made of a piezoelectric polymeric material and a therapeutic transducer made of a piezoelectric ceramic material, said second type being the other of said imaging transducer and said therapeutic transducer, said first transducer elements and said second therapeutic transducer element being connected to one another, said first transducer elements having different geometrical configurations taken from the group consisting of different sizes and shapes.

2. The device defined in claim 1 wherein said first transducer elements are piezoelectric ceramic transducer elements, said second transducer element being an imaging transducer element made of said piezoelectric polymeric material, said ceramic transducer elements being embedded in said second transducer element so that each of said ceramic transducer elements is spaced from the others of said ceramic transducer elements by said piezoelectric polymeric material.

3. The device defined in claim 2, further comprising an electrical circuit connecting said ceramic transducer elements in parallel to said imaging transducer element.

4. The device defined in claim 2, further comprising an electrical circuit connecting each of said ceramic transducer elements to an alternating voltage source.

5. The device defined in claim 2 wherein said piezoelectric ceramic transducer elements are electrically independent from each other and at least a subset of said piezoelectric ceramic transducer elements can be operated as a phased array while cross talk between members of said subset is minimized.

6. The device defined in claim 1 wherein said first transducer elements are piezoelectric polymeric transducer elements, said second transducer element being a therapeutic transducer element made of said piezoelectric ceramic material, said piezoelectric polymeric transducer elements being embedded in said therapeutic transducer element so that each of said piezoelectric polymeric transducer elements is spaced from the others of said piezoelectric polymeric transducer elements by said piezoelectric ceramic material.

7. The device defined in claim 6, further comprising an electrical circuit connecting said piezoelectric polymeric transducer elements in parallel to said therapeutic transducer element.

8. The device defined in claim 6, further comprising an electrical circuit connecting said piezoelectric polymeric transducer elements to an ultrasound signal processor.

9. The device defined in claim 6 wherein said piezoelectric polymeric transducer elements are electrically independent from each other and at least a subset of said piezoelectric polymeric transducer elements can be operated as a receiving array while acoustical and electrical cross talk between members of said subset is minimized.

10. The device defined in claim 1 wherein said at least one second transducer element is one of a plurality of second transducer elements all of said second type, said first transducer elements and said second transducer elements being bonded to one another so that each of said first transducer elements is spaced from the others of said first transducer elements by one or more of said second transducer elements and so that each of said second transducer elements is spaced from others of said second transducer elements by one or more of said first transducer elements.

11. The device defined in claim 10 wherein said first transducer elements are piezoelectric ceramic transducer elements and said second transducer elements are piezoelectric polymeric transducer elements, further comprising an electrical circuit connecting each of said ceramic transducer elements to an alternating voltage source, also comprising an electrical circuit connecting each of said piezoelectric polymeric transducer elements to an ultrasound signal processor.

12. The device defined in claim 1 wherein said at least one second transducer element is a therapeutic transducer element that is made of a piezoelectric ceramic material and that includes a plurality of recesses, grooves, holes, cuts, dimples, or indentations filled with said piezoelectric polymeric material.

13. The device defined in claim 1 wherein said at least one second transducer element is an imaging transducer element that is made of a piezoelectric polymeric material and that includes a plurality of recesses, grooves, holes, cuts, dimples, or indentations filled with said piezoelectric ceramic material.

14. The device defined in claim 1 wherein said first transducer elements and said at least one second transducer element constitute a dual-mode transducer module, said first transducer elements and said at least one second transducer element being electrically and acoustically independent of one another.

15. The device defined in claim 14, further comprising an electrical circuit connecting the elements of said dual mode transducer module, further comprising means for operating the elements of said module as an emitting and receiving array.

16. The device defined in claim 14 wherein said first transducer elements are therapeutic transducer elements made of piezoelectric ceramic material and electrically connected in parallel to one another and having respective resonance frequencies different from one another so as to permit selective activation of said therapeutic transducer elements.

17. The device defined in claim 14 wherein said first transducer elements are imaging transducer elements made of a piezoelectric polymeric material and electrically connected in parallel to one another and having respective frequency envelopes different from one another so as to permit selective processing of received ultrasound signals.

18. The device defined in claim 14 wherein said dual-mode transducer module includes at least one layer of piezoelectric polymeric material and at least one layer of piezoelectric ceramic substantially overlapping in a direction of ultrasound propagation.

19. The device defined in claim 18 wherein said layer of piezoelectric polymeric material and said layer of piezoelectric ceramic are separated by a water layer.

20. The device defined in claim 18 wherein said layer of piezoelectric polymeric material and said layer of piezoelectric ceramic collectively have a substantially planar or concave shape to produce a geometric focusing of ultrasound beam.

21. The device defined in claim 18 wherein said layer of piezoelectric polymeric material and said layer of piezoelectric ceramic are mechanically held together by means of an open cell metallic foam structure that permits water flow and efficient cooling.

22. The device defined in claim 18 wherein said layer of piezoelectric polymeric material and said layer of piezoelectric ceramic are poled in the same direction that permits an emission and reception of substantially unidirectional ultrasonic waves.

23. The device defined in claim 22 wherein said layer of piezoelectric polymeric material and said layer of piezoelectric ceramic are both poled in the direction normal to a surface comprising individual emitting and receiving element surfaces.

24. The device defined in claim 18 wherein said layer of piezoelectric polymeric material and said layer of piezoelectric ceramic are poled in different directions to enable a simultaneous emission and reception of substantially different ultrasonic waves to simultaneously monitor and induce the lesion formation.

25. The device defined in claim 24 wherein said layer of piezoelectric ceramic material is poled in the thickness mode normal to a surface comprising individual emitting and receiving elements surfaces and said layer of piezoelectric polymeric material is poled in a perpendicular direction radial to the center of said device in order to maximize the ability to perform multiwave imaging.

26. The device defined in claim 1 wherein said first transducer elements and said at least one second transducer element are integral parts of a unitary transducer module, further comprising means in contact with said module for deforming said module to thereby alter a focal point of transducer elements of said module that are therapeutic transducer elements made of said piezoelectric ceramic material.

27. The device defined in claim 26 wherein said means for deforming includes at least one bladder member.

28. The device defined in claim 26, further comprising an electrical circuit connecting to an alternating voltage source those transducer element of said module that are therapeutic transducer elements made of said piezoelectric ceramic material, also comprising an electrical circuit connecting said to an ultrasound signal processor those transducer element of said module that are imaging transducer elements made of said piezoelectric polymeric material.

29. A medical method comprising: providing an ultrasonic transducer device comprising a plurality of first transducer elements all of a first type and at least one second transducer element of a second type different from said first type, said first type being one of an imaging transducer made of a piezoelectric polymeric material and a therapeutic transducer made of a piezoelectric ceramic material, said second type being the other of said imaging transducer and said therapeutic transducer said first transducer elements and said second therapeutic transducer element being connected to one another to form a dual mode transducer module; placing said transducer module into effective wave-transmitting contact with a patient; energizing at least one of said first transducer elements and said second transducer element to produce an ultrasonic scanning waveform in a patient; monitoring signals produced by said at least one of said first transducer elements and said second transducer element in response to incoming ultrasonic pressure waves that are reflected and scattered by internal tissue structures of the patient, thereby detecting the incoming ultrasonic pressure waves; and energizing at least one of said first transducer elements and said second transducer element to treat organic tissues.

* * * * *